(12) United States Patent
Koptenko

(10) Patent No.: US 11,378,669 B2
(45) Date of Patent: *Jul. 5, 2022

(54) ANALOG STORE DIGITAL READ ULTRASOUND BEAMFORMING SYSTEM

(71) Applicant: Sergei V. Koptenko, Mississauga (CA)

(72) Inventor: Sergei V. Koptenko, Mississauga (CA)

( * ) Notice: Subject to any disclaimer, the term of this patent is extended or adjusted under 35 U.S.C. 154(b) by 41 days.

This patent is subject to a terminal disclaimer.

(21) Appl. No.: 16/747,149

(22) Filed: Jan. 20, 2020

(65) Prior Publication Data

US 2020/0225336 A1 Jul. 16, 2020

Related U.S. Application Data

(63) Continuation of application No. 15/681,573, filed on Aug. 21, 2017, now abandoned, which is a continuation of application No. 14/767,378, filed as application No. PCT/IB2014/000281 on Feb. 12, 2014, now Pat. No. 9,739,875.

(Continued)

(51) Int. Cl.
*G01S 7/52* (2006.01)
*A61B 8/00* (2006.01)
*A61B 8/08* (2006.01)
*A61B 8/14* (2006.01)

(Continued)

(52) U.S. Cl.
CPC .......... *G01S 7/52046* (2013.01); *A61B 8/145* (2013.01); *A61B 8/4483* (2013.01); *A61B 8/4494* (2013.01); *A61B 8/5207* (2013.01); *G01S 7/52023* (2013.01);

(Continued)

(58) Field of Classification Search
CPC ............ G01S 7/52046; G01S 7/52023; G01S 7/52047; A61B 8/145; A61B 8/5207; A61B 8/4494; A61B 8/4483; G11C 27/024; G10K 11/341

See application file for complete search history.

(56) References Cited

U.S. PATENT DOCUMENTS

| 4,271,488 A | 6/1981 | Saxe |
| 4,833,445 A | 5/1989 | Buchele |

(Continued)

FOREIGN PATENT DOCUMENTS

| WO | WO-2014125371 A1 * | 8/2014 | ........... A61B 8/5207 |
| WO | WO 20140125371 | 8/2014 | |
| WO | WO-2017106834 A1 * | 6/2017 | ............... A61B 8/00 |

*Primary Examiner* — Daniel Pihulic
(74) *Attorney, Agent, or Firm* — Blynn L. Shideler; Krisanne Shideler; BLK Law Group

(57) ABSTRACT

An analog store-digital read (ASDR) ultrasound beamformer architecture performs the task of signal beamforming using a matrix of sample/hold cells to capture, store and process instantaneous samples of analog signals from ultrasound array elements and this architecture provides significant reduction in power consumption and the size of the diagnostic ultrasound imaging system such that the hardware build upon ASDR ultrasound beamformer architecture can be placed in one or few application specific integrated chips (ASIC) positioned next to the ultrasound array and the whole diagnostic ultrasound imaging system could fit in the handle of the ultrasonic probe while preserving most of the functionality of a cart-based system. The ASDR architecture provides improved signal-to-noise ratio and is scalable.

20 Claims, 8 Drawing Sheets

Related U.S. Application Data

(60) Provisional application No. 61/763,929, filed on Feb. 12, 2013.

(51) Int. Cl.
   *G10K 11/34* (2006.01)
   *G11C 27/02* (2006.01)

(52) U.S. Cl.
   CPC ........ *G01S 7/52047* (2013.01); *G10K 11/341* (2013.01); *G11C 27/024* (2013.01)

(56) References Cited

U.S. PATENT DOCUMENTS

| | | |
|---|---|---|
| 5,722,412 A | 3/1998 | Pflugrath et al. |
| 5,997,479 A | 12/1999 | Savord |
| 6,126,602 A | 10/2000 | Savord et al. |
| 6,500,120 B1 | 12/2002 | Anthony |
| 6,705,995 B1 | 3/2004 | Poland et al. |
| 8,317,706 B2 | 11/2012 | Wegener |
| 8,545,406 B2 | 10/2013 | Magee |
| 9,739,875 B2 * | 8/2017 | Koptenko ........... G01S 7/52023 |
| 2008/0262351 A1 | 10/2008 | Scampini |
| 2010/0152587 A1 | 6/2010 | Haider et al. |
| 2010/0331689 A1 | 12/2010 | Wegener |
| 2011/0213251 A1 | 9/2011 | Robinson |
| 2011/0237953 A1 | 9/2011 | Olsson |
| 2012/0143059 A1 | 6/2012 | Magee |
| 2016/0011305 A1 * | 1/2016 | Koptenko ........... G01S 7/52047 367/7 |
| 2018/0003810 A1 | 1/2018 | Freeman |
| 2018/0003819 A1 | 1/2018 | Koptenko |
| 2018/0088219 A1 * | 3/2018 | Koptenko ............. A61B 8/145 |
| 2019/0133556 A1 | 5/2019 | Koptenko |
| 2019/0142383 A1 * | 5/2019 | Agarwal ................ A61B 8/469 600/437 |
| 2020/0187916 A1 * | 6/2020 | Koptenko ........... A61N 5/1049 |
| 2020/0225336 A1 * | 7/2020 | Koptenko ........... A61B 8/5207 |

\* cited by examiner

ANALOG STORE DIGITAL READ ULTRASOUND BEAMFORMING SYSTEM

RELATED APPLICATIONS

This application is a continuation of U.S. Patent continuation of U.S. patent application Ser. No. 15/681,573 filed Aug. 21, 2017, which published Mar. 29, 2018 as Publication Number 2018-0088219. U.S. patent application Ser. No. 15/681,573 is a continuation of U.S. patent application Ser. No. 14/767,378 filed Aug. 12, 2015, which published Jan. 14, 2016 as Publication Number 2016-0011305 and issued Aug. 22, 2017 as U.S. Pat. No. 9,739,875. U.S. patent application Ser. No. 14/767,378 is the U.S. National Phase of International Application PCT/IB2014/000281 which published as publication number WO 2014/125371 on Aug. 21, 2014. International Application PCT/IB2014/000281 claims the benefit of U.S. Provisional Patent Application Ser. No. 61/763,929, filed Feb. 12, 2013 entitled "Analog Store-Digital Read (ASDR) Ultrasound Beamformer Method and System." The above identified applications and patent are incorporated herein by reference.

BACKGROUND INFORMATION

1. Field of the Invention

The present invention relates to ultrasonic beamforming, more specifically the present invention relates to an analog store, digital read (ASDR) ultrasound beamforming system.

2. Background of the Invention

There are number of areas in the electronics field in which analog memory devices are being used successfully such as digital storage oscilloscopes, and in the physics field X-ray and charged-particle tracking applications. Some early predecessors of this technology can be traced to digital oscilloscopes and waveform capturing devices based on Fast-In-Slow-Out (FISO) principle such as one described in U.S. Pat. No. 4,271,488 entitled "High-Speed Acquisition System Employing An Analog Memory Matrix" or in U.S. Pat. No. 4,833,445 entitled "FISO Sampling System". These patents are incorporated herein by reference and the latter patent depicts the fast, high resolution FISO system, while the former describes an acquisition system that uses an analog memory matrix built of sample-hold cells arranged in rows and columns to form an M×N matrix that may be implemented on a single integrated-circuit (IC) chip.

The idea of a matrix analog memory device on IC was further developed by Stewart Kleinfielder who produced a range of multichannel transient analog waveform digitizer chips used to capture data from detectors in neutrino physics experiments, as well as by other contributors (for example, see Kleinfelder, S. A., "A 4096 Cell Switched Capacitor Analog Waveform Storage Integrated Circuit", IEEE Transactions on Nuclear Science, NS-37, No. 1, Feb. 1990.; and Kleinfelder, S. A., "Advanced Transient Waveform Digitizers," SPIE Particle Astrophysics Instrumentation Proc., v. 4858, pp. 316-326, August 2002.) Additional prior art representing informative background can be found in U.S. Pat. No. 5,722,412 entitled "Hand Held Ultrasonic Diagnostic Instrument"; U.S. Pat. No. 6,126,602 entitled "Phased Array Acoustic Systems with Intra-Group Processors"; U.S. Pat. App. Pub. No. 2008-0262351A1 entitled "Microbeamforming Transducer Architecture"; U.S. Pat. App. Pub. No. 2010-0152587A1 entitled "Systems and Methods for Operating a Two-Dimensional Transducer Array"; and U.S. Pat. APP. Pub. No. 2011-0213251A1 entitled "Configurable Microbeamformer Circuit for an Ultrasonic Diagnostic Imaging System." See also Haller, G. M.; Wooley, B. A., "A 700-MHz switched-capacitor analog waveform sampling circuit," IEEE Journal of Solid-State Circuits, v.29(4), pp. 500-508, April 1994. The above identified patents and published patent applications are incorporated herein by reference.

In medical diagnostic ultrasound, there were a number of attempts to use analog memory for ultrasound signal beamforming, notably U.S. Pat. Nos. 6,500,120 and 6,705,995, which are incorporated herein by reference. The process of ultrasound imaging, such as in medical diagnostic, begins with sending specially constructed ultrasonic signals (pulses, waves or wave packets) into the subject, e.g., tissues in medical diagnostics (or turbine blades for jet engine inspection, etc.) The pressure pulse propagates in depth while attenuating and scattering on the acoustic impedance interfaces (such as a boundary between different tissues) along the way. These scattered echoes are picked up by the receiving ultrasound array and from this data the tissue composition along the pulse propagation path is reconstructed as a single scan line. Then, the next pulse is sent into a different direction and the process of receiving scattered (or attenuated as in transmission tomography) ultrasound signals back to the sensor array, and the interpretation of the results is repeated until a required 2-D slice (B-mode frame) or a 3-D volume is assembled out of separate scan lines.

In order to increase the spatial and contrast (magnitude) resolution of a signal coming from the certain spatial location within the tissue, the ultrasound array needs to be focused on that location. Thus, in the course of pressure pulse propagation in the tissue, the receiving array needs to constantly shift its focus following the pulse current position. Therefore, one of the first steps in processing the raw data is called beamforming in which signals coming to different elements of the array are time-shifted before they will be added to one another. As a rule, the beamforming applies to both, transmit and receive signals.

FIG. 1 illustrates the first method used in forming ultrasound images, also known as analog beamforming. Generally, the ultrasound imaging device consists of an ultrasonic array 106 divided to a number of independent elements 107 or channels (typically to 64 or 128 elements in linear or curved 1D array). During the transmit stage of interrogation, the transmit beamformer sends variably delayed electric pulses to the elements of the ultrasound array 106. The relative delays between the signals is constructed in such a way that ultrasonic pulses emitted by elements 107 of the array 106 would arrive to the predetermined spatial point 100 (focal point P) simultaneously, with their phases aligned to achieve a coherent summation of wavelets coming from all elements 107 of the array 106. This wave would scatter at the point 100 and part of this spherical scattered wave would travel back to the elements 107 of the array 106. Each element 107 would convert pressure variations in the incoming wave into the voltage variation output 108. The portion of this scattered wave that reaches a face surface of an array element 107 can be seen as a wavelet 102 that travels along the ray 104 that connects the scattering point 100 and the face of the element 107. Depending on the mutual position of the scattering point 100 and the specific element 107 of the array 106, the path 104 would vary from the shortest one equivalent to radius $R_0$ 105 to the longest one. The spatial difference $\Delta D_i$ between the shortest path 105 and path from the point 100 to the i-element of the array 106 translates into the time delay $\Delta t_i$ between the arrivals of signals 108. The task of the receive beamformer is to modify the time differences between the signals 108 from all elements 107 participating in beamforming and sum them in accordance with the directions of the beamforming algorithm. For example, such a beamforming algorithm may require removing the time delays $\Delta t$ from all arrived signals and sum such processed signals (delay-sum algorithm), in effect focusing the array to the point P. It can be seen that workings of transmit and receive beamformers are mutually reciprocal, thus, describing the works of the receive beamformer is also a description of the solutions for the transmit beamformer.

The ways received signals are processed define the type of the beamformer. The analog beamformer shown on FIG. 1 was a first type of the beamformer used to process ultrasound signals. In it signals 108 were first amplified by voltage controlled amplifier (VCA) 110 to compensate the signal attenuation, then, a delay circuit 112 was used to time shift the signals to compensate the delays in arrival, then such aligned signals 114 were summed in analog summing circuit 116 and the output signal 118 was digitized by analog-digital converter (ADC) 120 producing output digital signal 122 that was stored in memory and used by the back end processor to reconstruct B-mode or Doppler images. The advantage of such design is the simplicity of the hardware. The disadvantages include poor time discrimination and low refresh rate of the analog design elements 112 (no dynamic beamforming) as well as irreversibility of the beamforming process such that only one beamforming algorithm can be applied to the captured signals.

The second common type of the beamformer used in ultrasound imaging is commonly known as the digital beamformer (see FIG. 2). In the digital beamformer, voltage signals 108 from the elements of the array 106 are amplified by the voltage controlled amplifier (VCA) 110 to compensate the signal attenuation, then, the signal in each channel is digitized at a certain sampling rate by channel ADC 124 that outputs digitized signal to the memory or First-In-First-Out (FIFO) registers where signals are shifted in accordance with the beamforming algorithm (for example such that to remove arrival delay $\Delta t$), then such processed digital data 128 from each participating channel are summed by digital summator 130 and output data 122 are written to the memory for further processing. The advantages of digital beamformer, such as shown in FIG. 2 are its speed and precision which allows implementation of the dynamic beamforming and the possibility of realization of multiple beamforming strategies on the same data volume. The disadvantage is complexity of the hardware; manifesting in larger hardware size, higher cost, and higher power consumption (heat generation).

For the reasons of clarity, the beamforming schematic for analog and digital beamformers shown on FIGS. 1 and 2 was simplified by removing the multiplexing stage. However in reality, as known to those of ordinary skill in the art, having the number of processing channels be equal to the number of the arrays' elements is a very expensive proposition. Thus, the array can have 64, 128, 256 or greater number of elements but the beamformer would have typically 32 or 64 channels and an analog multiplexing circuitry that would select elements of the array 106 into the current aperture. Also for the same reasons, cable and signal connectors that connect elements of array 106 to the analog front-end electronics are not shown, even though they do affect the cost and signal quality of the system.

From the description of the beamforming process it can be seen that the signal coming from the output of the array element 107 is processed independently from the signals coming from the other elements up to the output of the beamformer where all of the signals are combined. Thus, this text will refer to this signal path from the element 107 to the input of summator 116, 130 (or 136) as a "signal path" or "beamforming channel" or simply as "channel" 109.

As further background the international search report in PCT/IB2014/000281 identified that publications US2012-1433059 and US2010-0331689 and U.S. Pat. Nos. 8,545,406 and 8,317,706 were of general interest to the present invention and these patents and publications are incorporated herein by reference.

There remains a need in the art to reduce the size and power requirements of diagnostic ultrasound imaging and to utilize beamforming architecture to accomplish this goal.

SUMMARY OF THE INVENTION

This invention presents an Analog Store Digital Read (ASDR) ultrasound beamforming architecture which performs the task of signal beamforming using a matrix of sample/hold cells to capture, store and process instantaneous samples of analog signals from ultrasound array elements and this architecture provides significant reduction in power consumption and the size of the diagnostic ultrasound imaging system such that the hardware build upon ASDR ultrasound beamformer architecture can be placed in one or few application specific integrated chips (ASIC) positioned next to the ultrasound array and the whole diagnostic ultrasound imaging system could fit in the handle of the ultrasonic probe while preserving most of the functionality of a cart-based system. The ASDR architecture provides improved signal-to-noise ratio and is scalable.

One aspect of the present invention provides an Analog Store Digital Read ultrasound beamforming method for an ultrasound imaging system comprising the steps of: i) Providing an ultrasonic array formed of individual ultrasonic array elements configured for transmission and receiving; ii) Dividing the individual array elements into individual channels, wherein each channel comprises at least one array element; iii) Creating a receiving input signal for each channel from inputs received from each array element of the channel; iv) Sampling each receiving input signal for each channel at a sampling rate and storing the sampled data in a bank of sample-hold cells which are associated with that channel, wherein the bank of sample-hold cells form an analog random access memory for the sampled receiving input signal; v) Selecting at least one sample-hold cell data from at least one channel for each particular output time for each beamforming instance in accordance with a beamforming algorithm; vi) Summing all of the selected sample-hold cell data from the associated channels for the beamforming instance forming an analog beamformed received signal sample for the beamforming instance; and vii) Digitizing the analog beamformed received signal sample.

One aspect of the present invention provides an Analog Store Digital Read ultrasound beamforming system for an ultrasound imaging system comprising an ultrasonic array formed of individual ultrasonic array elements configured for transmission and receiving, wherein the individual array elements are formed into individual channels, wherein each channel comprises at least one array element and each channel uses less than 40 milliwatts in operation.

One aspect of the present invention provides an Analog Store Digital Read ultrasound beamformer for an ultrasound imaging system comprising: i) An ultrasonic array formed of individual ultrasonic array elements configured for transmission and receiving, wherein the individual array elements are grouped into individual channels, wherein each channel comprises at least one array element; ii) A Receiving input signal control circuitry for creating receiving input signals for each channel from inputs received from each array element of the channel; iii) A plurality of banks of sample-hold cells with each bank of sample-hold cells associated with one channel, wherein the beamformer is configured for sampling each receiving input signal for each channel at a sampling rate and storing the sampled data in one bank of sample-hold cells which are associated with that channel, wherein the bank of sample-hold cells form an analog random access memory for the associated sampled receiving input signal; iv) A beamforming processor configured for selecting at least one sample-hold cell data from at least one channel for each beamforming instance in accordance with a beamforming algorithm; v) An analog summation element for summing all of the selected sample-hold cell data from each channel for each beamforming instance and forming an analog beamformed received signal sample for the beamforming instance; and vi) An Analog-to-Digital converter for digitizing the analog beamformed received signal.

These and other advantages of the present invention will be clarified in the brief description of the preferred embodiment taken together with the drawings in which like reference numerals represent like elements throughout.

DESCRIPTION OF THE PREFERRED EMBODIMENTS

The present invention relates to ultrasound diagnostic systems, such as used in medical diagnostic systems for medical human and animal applications. The system and method of the present invention is also applicable to non-destructive testing/evaluation (e.g., pipeline testing, airframe testing, turbine blades testing, bridge and structural testing, manufacturing testing (e.g. metal working rolls)) Ultrasonic testing is a type of nondestructive testing commonly used to find flaws in materials and to measure the thickness of objects. Frequencies of 1 to 50 MHz are common but for special purposes other frequencies are used. Inspection may be manual or automated and is an essential part of modern manufacturing processes. Most metals can be inspected as well as plastics and aerospace composites. Lower frequency ultrasound (50-500 kHz) can also be used to inspect less dense materials such as wood, concrete and cement. The system and method of the present invention is also applicable to geophysical exploration and sonar applications, and generally any ultrasound imaging (or image-like) applications requiring beamforming for transmission and/or receiving. The present invention is directed in particular the way signals coming from the elements of an ultrasonic array (receive beamformer) and going to the elements of the same array (transmit beamformer) are treated. The invention describes an improved beamformer system that provides better image quality combined with significant reduction in systems' size, power consumption and production cost as compared to current systems. Thus, even though the main area of application of this invention is in medical ultrasound, this beamforming architecture and the hardware and software built upon its principles can be used in other areas such as non-destructive testing, sonar, radar, terahertz, infrared, optical imaging systems or for seismic geophysical exploration, just to name a few examples.

The general idea of the new design is to create a mixed beamformer that would use digital control and manipulation of analog signals from the transducer array elements. Such design allows radical minimization of the hardware volume and power consumption of electronic circuitry, opening a possibility for the development of portable and ultraportable ultrasound machines as well as advances in premium systems, as described in detail below.

Figure 1:
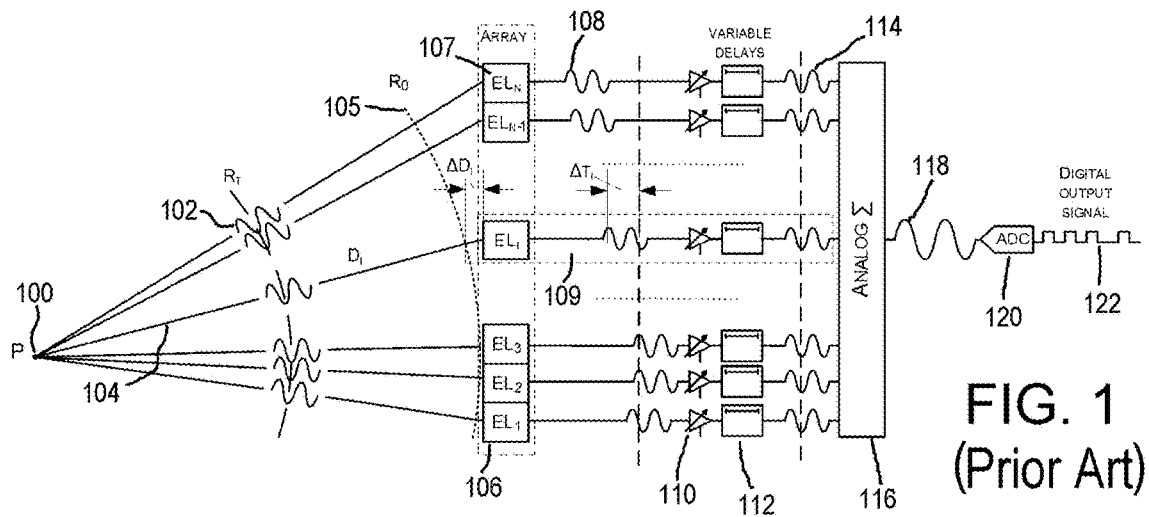
FIG. 1 is a schematic representation of a prior art analog beamformer.
Figure 2:
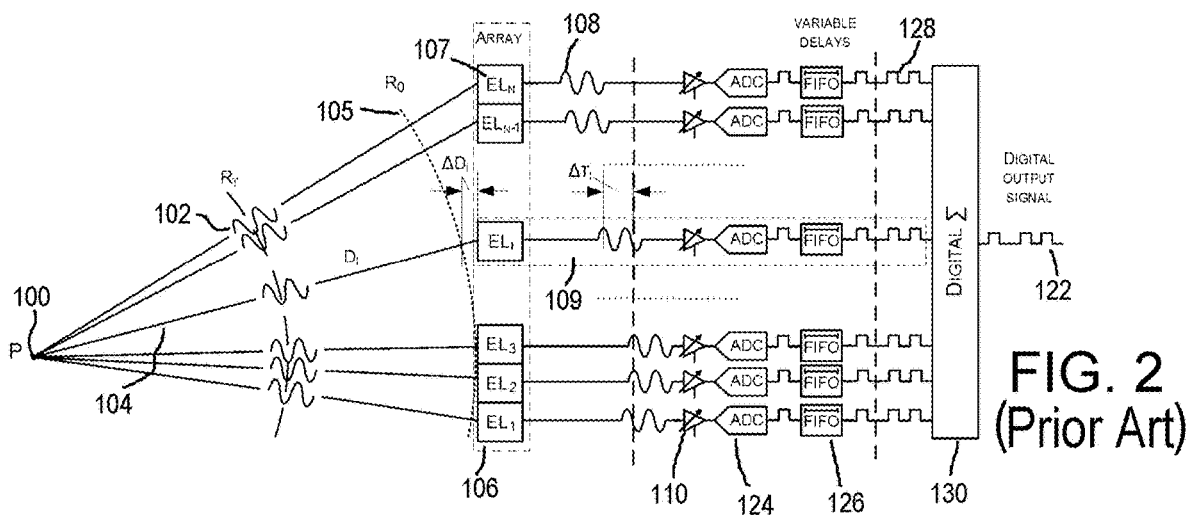
FIG. 2 is a schematic representation of a prior art digital beamformer.
Figure 3:
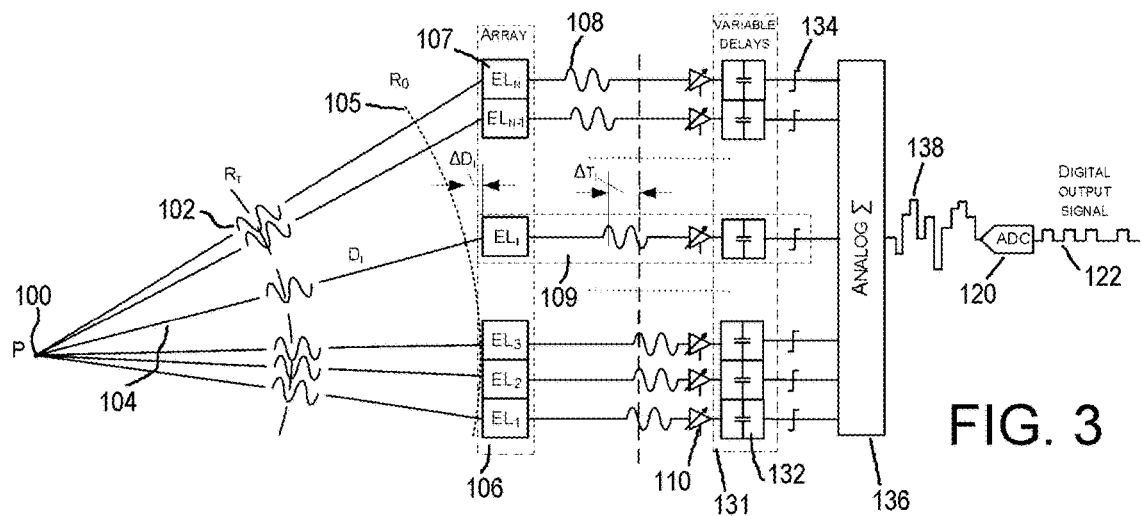
FIG. 3 is a schematic representation of an Analog Store Digital Read (ASDR) ultrasonic beamformer in accordance with one embodiment of the present invention.
Figure 4A:
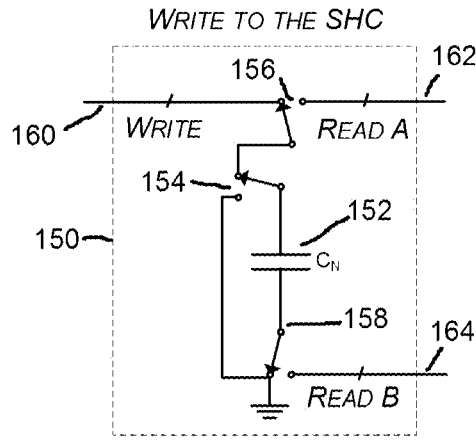
FIGS. 4A-D are schematic representation of representative Sample/Hold Cells (SHC) for use in the ASDR ultrasonic beamformer of the present invention.
Figure 4B:
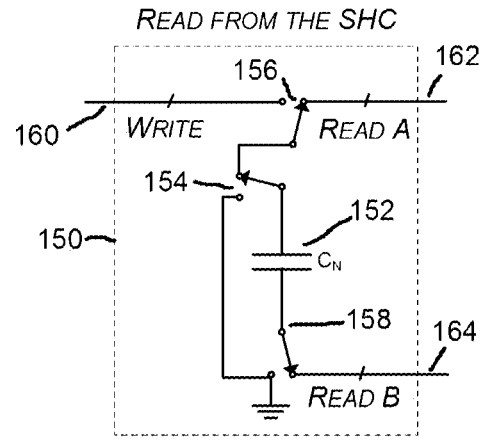
Figure 4C:
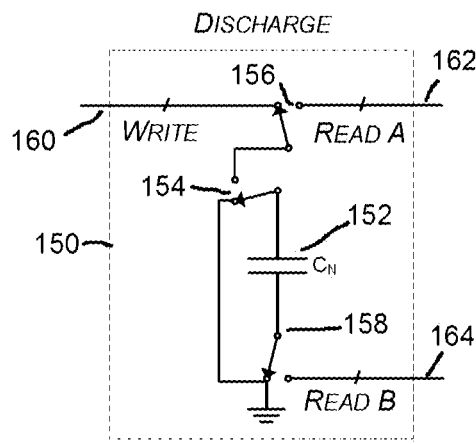
Figure 4D:
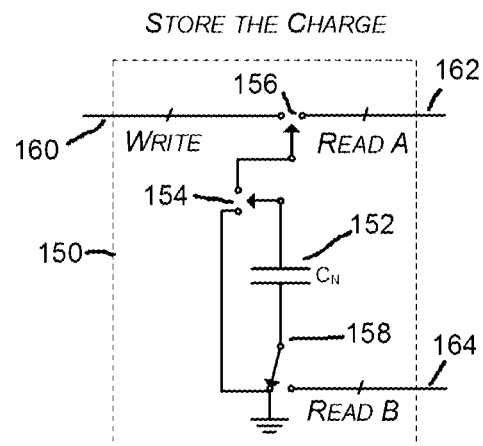

FIG. 3 depicts a schematic outline of a proposed new type of the beamformer. In the beamformer of the present invention, an analog signal 108 from the element 107 of the array 106 goes through a voltage controlled amplifier (VCA) 110 to compensate the signal attenuation in the media, then is written into an array 131 of Sample-Hold Cells and at a certain sampling rate as a sequence of voltage levels. The sampling rate may be fixed or variable and also may be independent and different from the sampling rate of the reading from the sample hold cells of array 131.

Each SHC array 131, also known as Analog Random Access Memory (ARAM) array 131, consists of a plurality Sample/Hold Cells 150 arranged in distinct rows or banks 132 and that have common signal lines and control switches that function in a fashion similar to conventional digital random access memory as it will be discussed below. Next, in each signal channel 109, one Sample/Hold cell 150 of one row 132 is selected in accordance with the beamforming algorithm and the samples of analog signal 134 from all channels participating in the beamforming process at this particular time moment, also known as beamforming instance which being defined as one sampling step in execution of the beamforming algorithm, are summed by an analog summing circuit 136. The output analog signal 138 which represents the results of the beamforming as a sequence of analog samples is digitized by the analog-digital converter 120 and output data 122 is written to the memory for further processing.

In other words, the beamforming process consists of storing analog samples of continuous signals from array elements, then reading the content of certain analog memory cells in the same way that digital memory cells are read in the digital beamformer process. However, instead of adding digital representations of signals to produce the output beamformed signal, the analog representations of the same signal are summed up first and the result is digitized. Thus, the process of operating samples of analog signals in a digital manner comprises the essence of the Analog Store-Digital Read (ASDR) ultrasound beamformer system and method of the present invention.

In order to describe the functions and operations of the Analog Store-Digital Read (ASDR) ultrasound beamformer the description will begin with the basic building blocks of such the device and progress up to the system level.

Sample—Hold Cell

The basic building block of the analog memory array is a Sample-Hold Cell (SHC). The design of SHC is well known and comprises the prior art. Here a SHC design is used based on the storage capacitor as an example of the design; however, any device that can store an analog quantity can be used for building such a cell.

The schematic organization of a single sample-hold cell (SHC) 150 is shown on FIGS. 4A-D and 5. Main elements of the SHC are the storage capacitor 152, analog switches 154, 156 and 158 that connect capacitor 152 to input analog signal line WRITE 160 and output signal lines READ A 162 and READ B 164, or to the ground. Switches 154-158 can be made based on transistors, MEMs, or other technology enabling analog switching and multiplexing.

Figure 5:
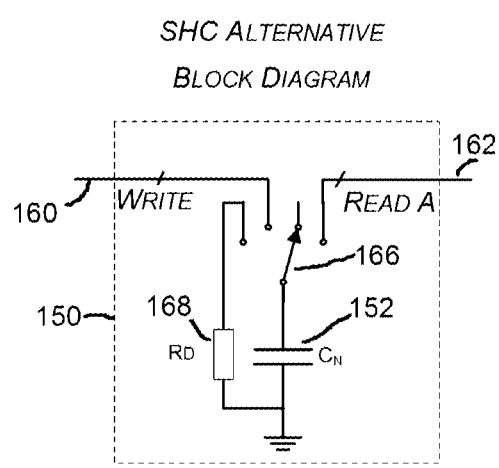
FIG. 5 is a schematic representation of an alternative SHC for use in the ASDR ultrasonic beamformer of the present invention.

FIG. 5 illustrates schematic representation of variations in the basic SHC 150 design, such as the use of one multi-position switch 166, an addition of bleed resistor 168 to control the capacitor discharging process or the removal of the READ B signal line, and joining the bottom plate of the storage capacitor 152 permanently to the signal ground. These or any other variation of the SHC design are included as prior art.

Figure 6:
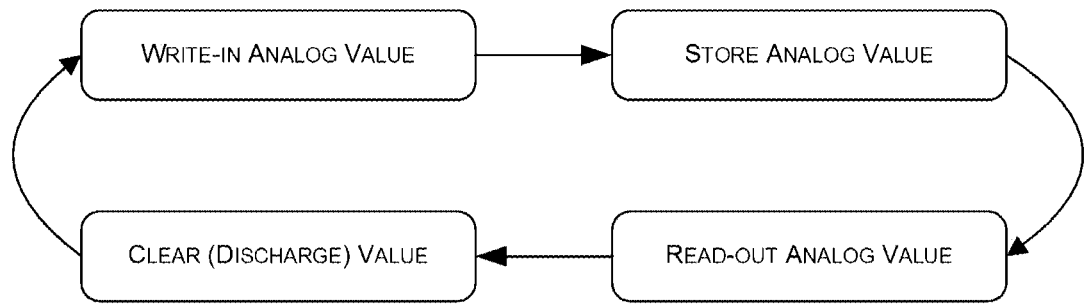
FIG. 6 is a schematic timing diagram illustrating work of the Sample/Hold Cells used in the ASDR ultrasonic beamformer of the present invention.

The SHC 150 working cycle, shown schematically in FIG. 6, consists of the following operation: writing the voltage level into the storage capacitor 152, storing the charge, reading the content of the capacitor 152, and erasing the content of the storage capacitor 152 in preparations for the next work cycle. Referring to time diagram of FIG. 7, during the write operation at time $t_i$, the top plate of the capacitor 152 is connected to the input analog signal line WRITE 160 via switches 154 and 156. Switch 158 connects the bottom plate of the 152 to the ground. The voltage value of $V(t_i)$ from the output of $VCA_1$ (110) is stored in the capacitor 152. During the time period $T_3$ (storage operation), one or both switches 154 and 156 are in a high impedance state (open or disconnected from signal lines). After time $T_3$ that occurs within the time period $T_1$, the content of capacitor 152 is read. In the read operation, switch 158 connects the bottom plate of the capacitor 152 to the READ B output signal line 164 and the top plate of the capacitor 152 through switches 154 and 156 is connected to the READ A signal line 162. The discharge operation that occurs during time period $T_2$ consists of connecting the top and bottom plates of the capacitor 152 via switches 154 and 158 to the ground directly or through the bleed resistor 168. The total time of read-store-discharge cycle (referring to FIG. 7) $\Delta t = t_{i+1} - t_i = T_1 + T_2$ is defined by the length of the rows (number of S/H cells) of SHC bank 109, sampling rate, and the maximum signal delays need to be corrected.

The open and close state of switches 154-158 is controlled by the beamformer control circuitry that will be discussed below.

Sample-Hold Cell Array

The separate sample-hold cells 150 are organized row-wise and column-wise into the Sample-Hold Cells Array 131 (or an analog random access memory or ARAM). In the preferred embodiment the number of rows 132 of the array 131 (or a number of beamformer channels 109) is typically equal to the number of elements 107 in the transducer array 106 (for example 128 elements). In other embodiments, the number of beamforming channels 109 can be smaller or larger that number. The number of columns (number of S/H cells in SHC bank 132) is defined by the sampling rate and the maximum delay in signal arrival to the elements of the transducer array 106 as it will be explained later.

For example, for a common curved medical ultrasound transducer array like that known as C5-2/60 with a fully opened active aperture of 128 elements (total length of 60 mm) and the signal penetrated into the tissue to z=100 mm depth, the maximum signal path difference (a pulse coming from the depth z to the center of the aperture and to the aperture edge) will be around $\Delta d \approx 4.4$ mm (see FIG. 3 for the reference). At a sound speed of 1540 m/s, it gives maximum delay $\Delta t \approx 2.86 \times 10$-6s. At the sampling rate of S=40 MS/s (mega samples per second) it will be necessary to capture a minimum 114 sample points to be able to compensate for the 2.86 micro-seconds delay in arrival of signals to all elements 107 of the aperture. Thus, in this particular case, the SHC array 131 will consist of at least 114 columns of sample-hold cells 150 in each of 128 rows 132. In other embodiments the number of columns N can be bigger than the minimum required number, but the criteria N>$\Delta t \times S$ (Samples/sec) gives the minimum estimate for the number of sample capacitors or cells 150 in each row 132.

Figure 8A:
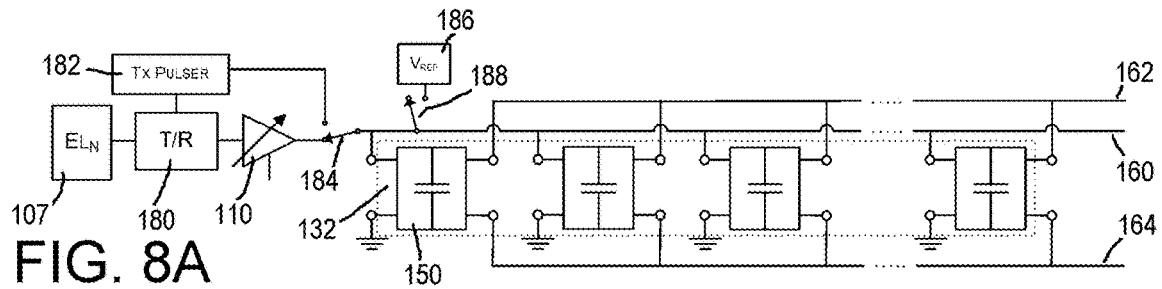
FIGS. 8A and 8B are alternative schematic block diagrams of transmit and receive beamformer channel 109 in accordance with two embodiments of the present invention.
Figure 8B:
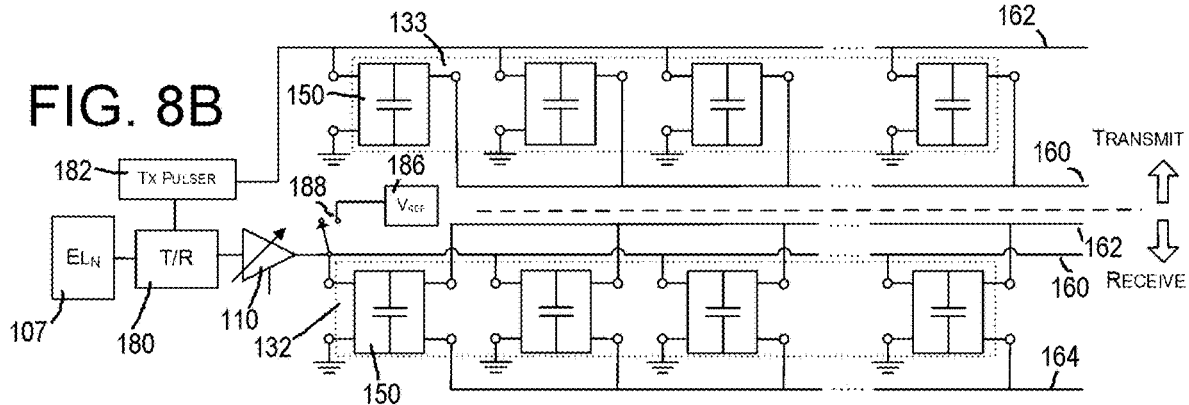

Column-wise organization of the SHC array is used for writing data into the S/H cells 150 and row-wise organization is used to read data out of the cells. In FIGS. 8A and B, two main architectures/methods to employ such an array in an ultrasound beamformer are shown. FIG. 8A displays a partial schematic diagram of one channel 109 of an ultrasound system in which a SHC row 132 is shared between the transmit and receive beamformer channel via switch 184 and FIG. 8B shows a partial schematic diagram of one ultrasound channel 109 where transmit and receive beamformers have their own SHC row banks 132 and 133 to store and read analog samples. Note, that even though banks 132 and 133 may have the same design (as shown on FIGS. 4A-D and 5), the SHC bank 133 is marked separate from the 132 just to denote that they belong to two physically different arrays that may have different size and different values of storage capacitors 150. All S/H cells 150 that belong to the row bank 132 are connected to common signal lines 160, 162, and 164. The logic circuits that control cells switches 152-158 allow selection of a single cell, a group, or all cells to perform read, write, store, or discharge operations in a similar fashion to the logic that controls the digital dynamic RAM operations.

Transmit Beamformer Operations

Referring to the FIG. 8B, the transmit phase of beamformer operations begins with writing a pulse shape into the beamformer channel transmit analog sample storage 133 in which the Digital Analog Converter or DAC (not shown) uses WRITE line 160 to write voltage level samples into cells 150 of SHC row 133. The preferred embodiment is to have a number of transmit beamformer channels 133 be equal to the number of receive channels 132 and the number of the transducer array elements 107. In other embodiments, a number of transmit channels can be bigger than the number of array elements for storing different signal shapes or smaller than the number of elements 107 down to a single channel 133 serving all elements of the array. The pulse shape is formed by a sequence of voltage samples stored in 133. In order to form the pulse, sample-hold cells 150 of SHC row 133 are sequentially connected to the input of high voltage pulser 182 that is in turn connected to the transducer element 107 via transmit-receive switch 180. The pulse central frequency and the frequency content are defined by the pulse shape together with the sampling (or clock) speed at which voltage samples arrive to the input of the pulser 182. The beamforming delay for the each transmit channel is formed by the channels' own hardware or software timer that delays the start of pulse forming by an appropriate number of clock cycles using for example a countdown counter or buffer.

In one embodiment, the voltage resolution of the sample-hold cells in the SHC row of transmit channel 133 can be lower than the SHC resolution in the SHC row of receive channel 132. In other embodiments, transmit channel cell resolution can be as low as 2 bits or be as high as the receive SHC resolution. The depth of the transmit SHC row 133 can vary from two cells to the number equal of the number of cells in the receive row 132.

The SHC row 133 may store not one but a number of pulse shapes sequentially, that can be rapidly selected by the transmit controller to form different pulses during the current scan line operation (for instance to form multiple focus points in one scan line generation with various central frequency pulses) or for a different scan lines generations (for example as in pulse inversion imaging).

In one embodiment, each SHC row 133 may store a pulse shape that is common for all beamforming channels or store a pulse shape that is individual for each beamforming channel or groups of beamforming channels.

The pulse shapes can be refreshed or re-written during the receive phase of beamforming if required. The clock or sampling frequency of the transmit beamformer circuitry can be the same as clock speed of the receive beamformer or be different from it, either higher or lower—i.e. they are independent. Further the sampling frequency may be variable. In one embodiment, the sampling speed of the transmit beamformer can be changed programmatically while in transmit to change the frequency content of the transmit pulse while preserving its' recorded shape.

The other possible embodiment of transmit-receive channel architecture is shown in FIG. 8A. In this embodiment, transmit and receive parts of beamforming channel share the same SHC array 132 via switch 184. The transmit and receive operation in this embodiment proceeds in the same fashion as it was described above with the exception that at the end of receive cycle the WRITE line 160 is disconnected from the output of 110 and a pulse shape data from the external DAC is written sequentially into SHC cells of array 132 while the last receive beamforming events occur in the far end of the SHC array.

Receive Beamformer Operations

Referring to the schematic of the beamforming channel 109 on FIG. 8B, the piezo-element 107 (part of the transducer array 106) converts electric energy into mechanical vibrations during the transmit stage and mechanical vibration energy into electric signals during the receive stage. The transmit-receive switch 180 connects the element 107 to the output of high voltage transmit pulser 182 or to the input of the amplifier 110 (that may internally consist of a low-pass filter, a low noise amplifier (LNA) stage and a VCA as a second stage for time-gain compensation). The filtered and amplified signal from the output of the VCA 110 is connected to the WRITE signal lane 160 that connects all sample-hold cells 150 that form the SHC row 132. Instead of the output of VCA 110, the signal line 160 can be connected via switch 188 to the reference voltage source 186 which allows testing the performance and calibration of cells in the bank 132 by writing and reading the calibrated voltage levels. Output READ signal lines 162 and 164 allow connecting any storage capacitor of any cell 150 to the input of the current or voltage follower or a summing circuit or allow to directly connect selection of storage capacitors 150 sequentially when no apodisation is required (for example, in sub-aperture beamforming).

Figure 7:
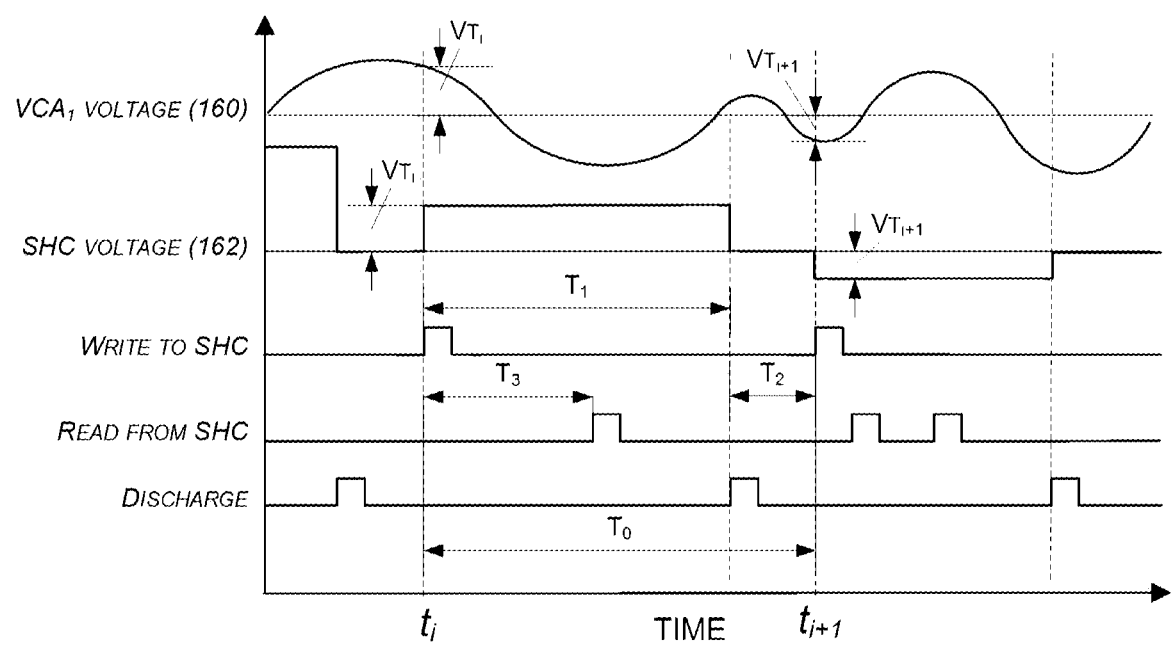
FIG. 7 is a timing diagram illustrating work of the ASDR ultrasonic beamformer of the present invention.

During the receive stage, voltage levels from VCA 110 are sampled with a certain frequency (sampling rate) and stored in consecutive cells 150 until the last cell has received a sample to store. At that point, the write operation starts again with the first cell (proceeding by the cell discharge operation as shown in FIGS. 6 and 7). In some embodiments the discharge operation may not be included and the old cell's content is simply replaced by the new one during the write operation. The writing operation begins at the moment when the signal scattered from the minimum depth set by the user reaches the array and continues until the signal from the pre-set maximum depth comes to the farthest element of the array participating in beamforming. However, instead of writing and storing the whole time-pressure history for all elements of array in the course of receiving scattered data for the creation of a scan line, the present invention uses a sliding window approach, storing only the current part that is used in the creation of current samples of the beamformed signal.

Figure 9:
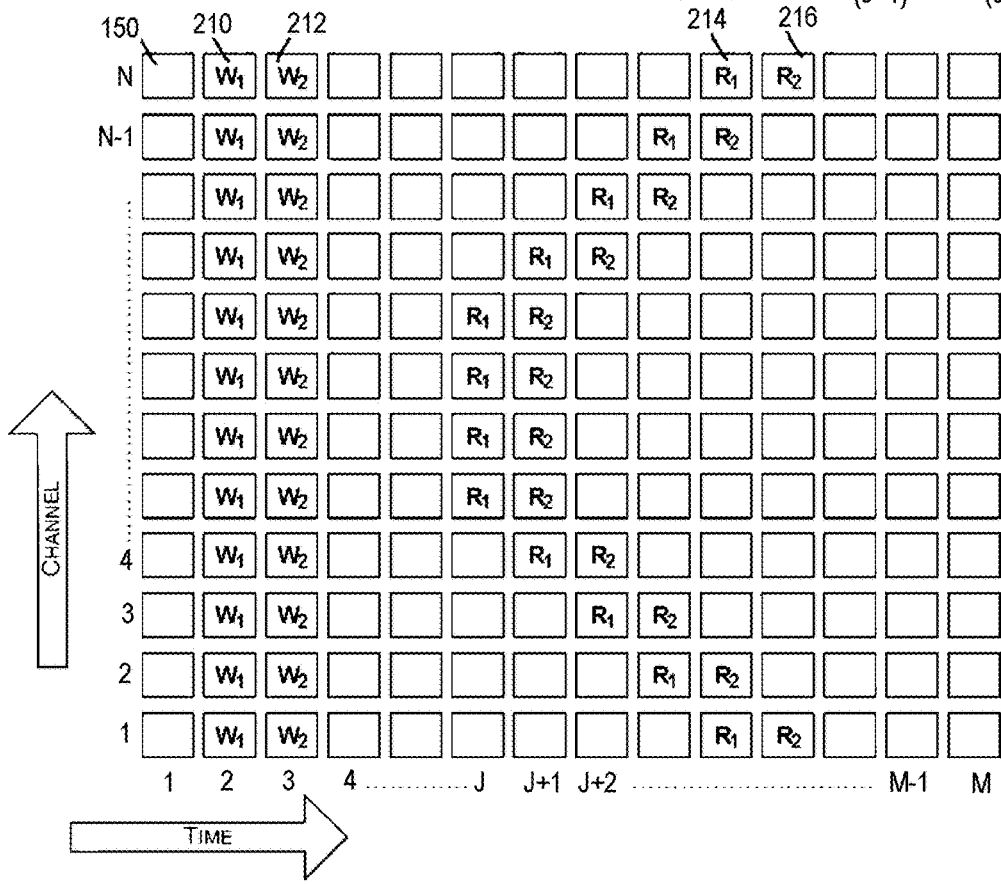
FIG. 9 schematically illustrates the process of writing to and reading from the SHC array used in the ASDR ultrasonic beamformer of the present invention.

After the start of data acquisition and filling enough columns, the reading (beamforming) operation begins. FIG. 9 illustrates how the writing to and reading from the SHC array occurs. In it, each square represents one sample-hold cell 150 with N rows (beamforming channels) and M columns. At time instance $t_{J+1}$ samples of voltage levels from corresponding VCAs 110 are written into column 210 marked by the symbol $W_1$. At the same time, cells 214 marked by $R_1$ are selected by the beamforming algorithm for a creation of the current output beamformed sample. The content of these cells is read and summed by a summing circuit. At the next sampling interval time $t_{J+2}$ S/H cells 212 marked by $W_2$ are written and cells 216 ($R_2$) are read. When the read operation reaches the end of the SHC array it folds over to the first column, in the same way as the analog sample write operation does. Since the present system has separate signal lines for read and write, these operations could be done simultaneously. It is desirable to keep the number of columns in the array a bit bigger than the minimum number required, so the read and write operation would not overlap. In some embodiments the system divides the whole array 131 column-wise into a few independent blocks allowing a write operation in one column-wise memory block, discharge in the next one, while the rest of blocks is reserved for the read operation. For instance, the system divides column-wise the array 131 consisting of 128×128 elements into eight blocks of 128×16 SHC cells each. Then, at some moment of time block 5 is used for writing data from 128 channels, block 6 for discharging it's content, and blocks 7, 8, 1-4 are used for reading and beamforming. This way we can use a segmented single signal line for accessing the cells instead of separate read and write lines.

The freedom in selecting which cells would participate in the beamforming instance allows reusing the stored sampling data to implement not just a single beamforming algorithm, but obtain a number of various beamforming scenarios on the same block of data, similarly as it can be performed with stored channel data in digital beamforming architecture.

Generally speaking, write operations do not need to be performed on consecutive columns of S/H cells. The cell's addresses can be random as long as the memory controller keeps the score. Writing data column-wise is a convenient option, however SHC arrays can be also built to be used as truly random access analog memory ARAM with voltage level samples from an element being stored in random locations (no hard channel and timing links). Potential advantages of that approach are enabling freedom to choose the depth of SHC row banks (channels) and size of aperture (number of rows or transducer elements). Among potential disadvantages-analog multiplexors are needed to switch channels and the writing speed may be lower, however, such a design option may be considered for some applications.

Also, sampling rates for Sample-Hold Cells array 132, summator 136 and ADC 120 does not need to be the same and/or be synchronized. In some embodiments it may be desired to have a single clock to control all three blocks, in other embodiments it may be desired to have a phase difference between read, write and digitize operation. In yet another embodiment it may be desired to have different frequencies phase-linked or completely independent, to control the operation of Sample-Hold Cells array 132, summator 136 and ADC 120. There may be benefits (e.g., anti-aliasing) to have all three functional blocks functioning at independent sampling rates with different frequencies and phases. For instance, writing data 108 from the elements 107 could be done at 100 mega samples per second, reading data 134 for summation 136 at 85 mega samples per second and digitizing by ADC 120 at 60 MS/s.

Receive Beamforming Summing Operations

Figure 10:
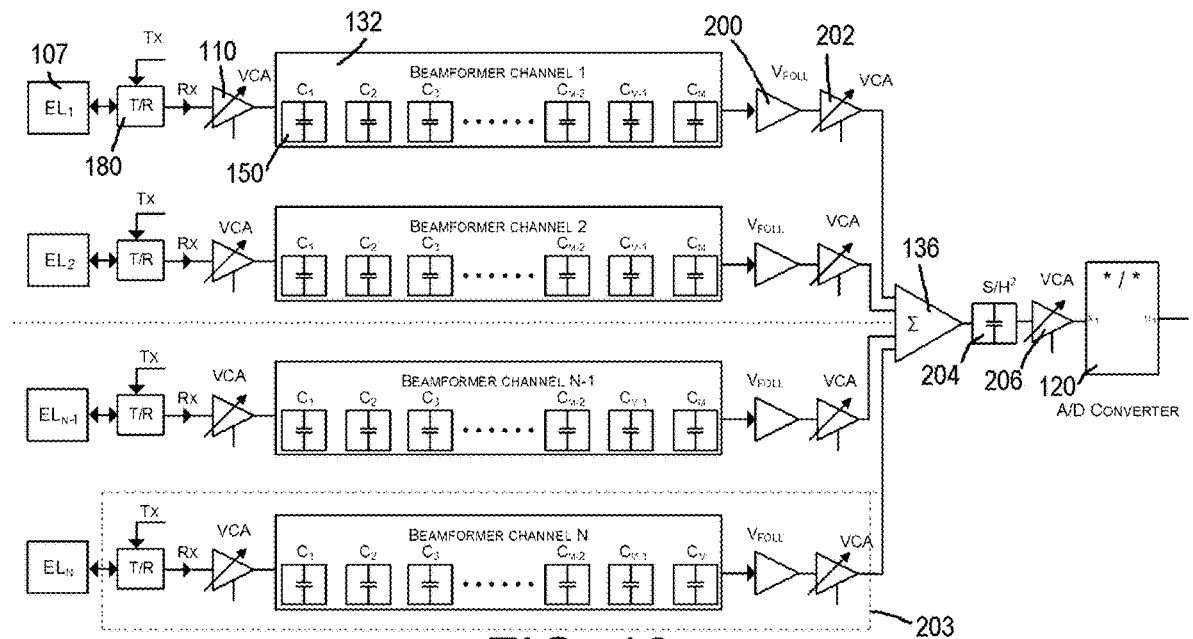
FIG. 10 is a schematic representation of a receive beamformer used in the ASDR ultrasonic beamformer of the present invention.

The beamforming summation can be done with voltage or with current values of analog samples stored in SHC 150. Referring to FIGS. 9 and 10, in the beamforming instance at time $t_{j+1}$ after cell 150 (marked by $R_1$) in each beamforming channel 132 was selected by the beamforming algorithm, the storage capacitor 152 is connected to the input of voltage or current follower 200 by signal lines READ A (162) and READ B (164). In one embodiment, the voltage follower 200 is connected to voltage controlled amplifier 202 that is used for forming of aperture apodization and for capacitor calibration compensation. The current active aperture span is controlled by setting apodization value to zero for the channels that will not be participating in current beamforming instance. In another embodiment, voltage follower 200 and VCA 202 can be combined in one circuit. In yet another embodiment, 200 is a current follower. In another embodiment one plate of storage capacitor 152 is permanently attached to the signal ground and signal line READ B 164 is absent.

In one embodiment each receive beamforming channel has its own 200 and 202 amplifiers. Another embodiment may have a reduced number of 200 and 202 amplifiers and have analog multiplexors to connect the selected beamforming channels with the aperture formed by the multitude of 200 and 202 amplifiers. Yet another embodiment may have VCA 202 be removed or be replaced by an analog switch for active aperture selection.

For the convenience, the system defines the analog channel AC 203 that includes all of the elements and functional blocks that participate in the analog signal acquisition, storing and processing from the output of array element 107 to the voltage sample on the output VCA 202. Output of VCA 202 (or AC 203) represent a properly delayed, apodized and compensated analog channel sample.

In the voltage summing scheme, the summing circuit 136 receives instances of voltage samples from all beamforming channels, sums them and outputs the result. If the current summing approach is used, the circuit 136 is the current summing circuit. In another embodiment summing is achieved not with the content of actual storage capacitors 152 but their content first copied into temporary storage capacitors that are used for summing. In yet another embodiment, summing is achieved by connecting all storage capacitors 152 or temporary storage capacitors participating in the beamforming event serially in which line 164 of the first capacitor is connected to line 162 of second row capacitor etc. until the last capacitor is connected. The sum value then read from line 162 of the first capacitor and line 164 of the last capacitor.

The output of the summing circuit 136 is connected to a secondary Sample-Hold Cell 204, VCA 206, and Analog-Digital Converter 120. The output of analog digital converter 120 is a digitized beamformed RF signal. Elements 204 and 206 may be absent from the schematic, be attached in reverse order, or be internal elements of ADC 120. The VCA 206 may include a low pass filter.

In one embodiment, in-phase/quadrature (I/Q) data is generated by directly sampling the received radio frequency (RF) signal from the output of ADC 120. In another embodiment the output of VCA 206 also may be connected to a conventional I/Q demodulation sampling circuit.

Secondary SHC

Figure 11:
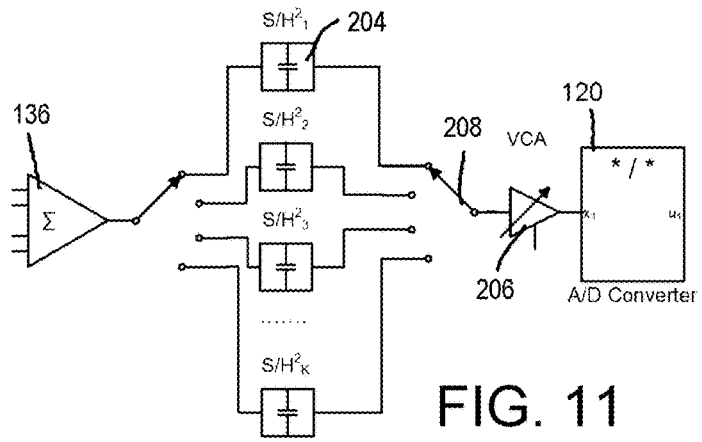
FIG. 11 is a schematic block diagram of a second stage Sample/Hold Cell array in accordance with one aspect of the present invention.

The secondary Sample-Hold Cell 204 has the same design as S/H cell 150. In one embodiment a single SHC 204 is used to store the current results of summing in element 136. In another embodiment, as shown on FIG. 11, a number of S/H cells can be used for temporarily storing results of summing the different beamforming algorithms working on the same channel's data block before their analog to digital conversion via switch 208 and secondary VCA 206 (VCA may be absent or replaced by a voltage follower). In yet another embodiment, the secondary SHC array may have a similar size and a similar use to the primary SHC array 131. In it, primary array 131 is used for sub-aperture beamforming, operating on the group of closely spaced transducer elements and the secondary SHC array is used for beamforming the results of pre-beamforming as described below. In yet another embodiment there may be a tertiary SHC array working on results of sub-aperture beamforming of the secondary SHC array and so on.

1.5D, 1.75D, 2D Arrays Operation

Figure 12:
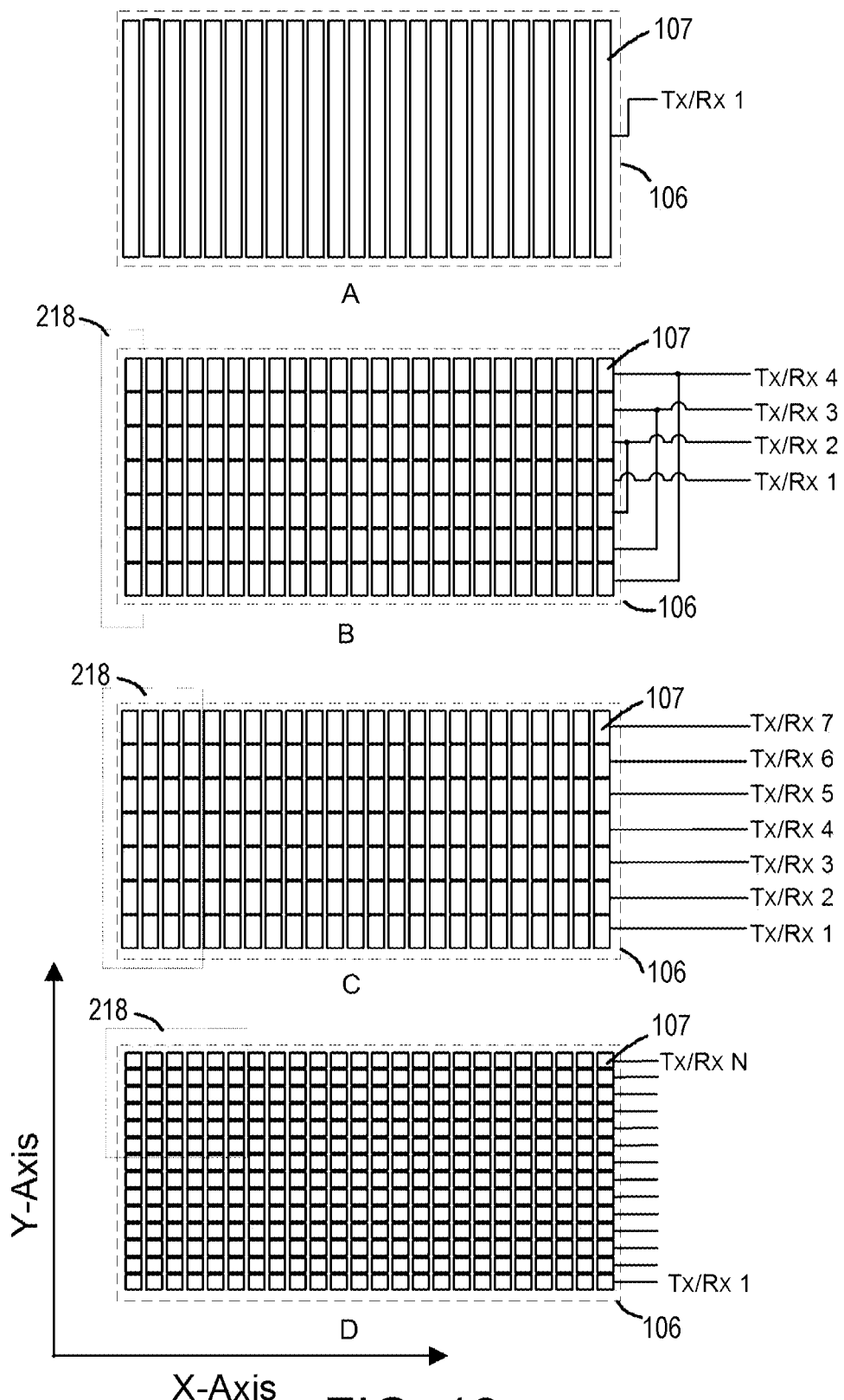
FIG. 12 is a schematic composition of common arrays.

The beamforming architecture described above can accommodate any common 1D ultrasound arrays with number of elements (transmit-receive channels) in array going up to a few thousand (refer to FIG. 12A schematically picturing layout of a common 1D array). With a larger element count or with a more complicated structure of the transducer array, being 1.5D, 1.75D, or 2D, this basic architecture can be adapted in the way partially described above (secondary Sample-Hold Cell array). Referring to the top schematic of FIG. 12, the typical 1.5D or 1.75D array is essentially a 1D transducer that has its elements divided in elevation directions with each element preferably having separate beamforming channels. The number of divisions can be any, however when the size of the sub-element in elevation direction (Y-axis on the figure) approaches the size in axial direction (X-axis) and both sizes being equal or less than half of wavelength of the array's central frequency, it is more proper to describe such array as a 2D array (referring to lower schematics of FIG. 12 correspondingly). The main reason for using such an array is that it allows controlling focusing in elevation direction in the same way the axial focusing is controlled, thus, providing constant image slice thickness in elevation with corresponding improvements in contrast and detail resolution.

The main difference between 1.5D and 1.75D arrays is that in 1.5D array elements are connected symmetrically column-wise (referring to FIG. 12) so the elevation focusing is done only in the plane of the image slice or in the Y-Z plane (Z-axis being a depth and directed perpendicular to the FIG. 12 plane) while 1.75D array sub-elements are controlled independently, thus, a limited out-of-plane focusing can be performed, restricted by the grating lobes position. The 2D array, with its elements being close to ½ wavelengths, has the same freedom in focusing in all three directions: elevation, axial, and depth.

Figure 13:
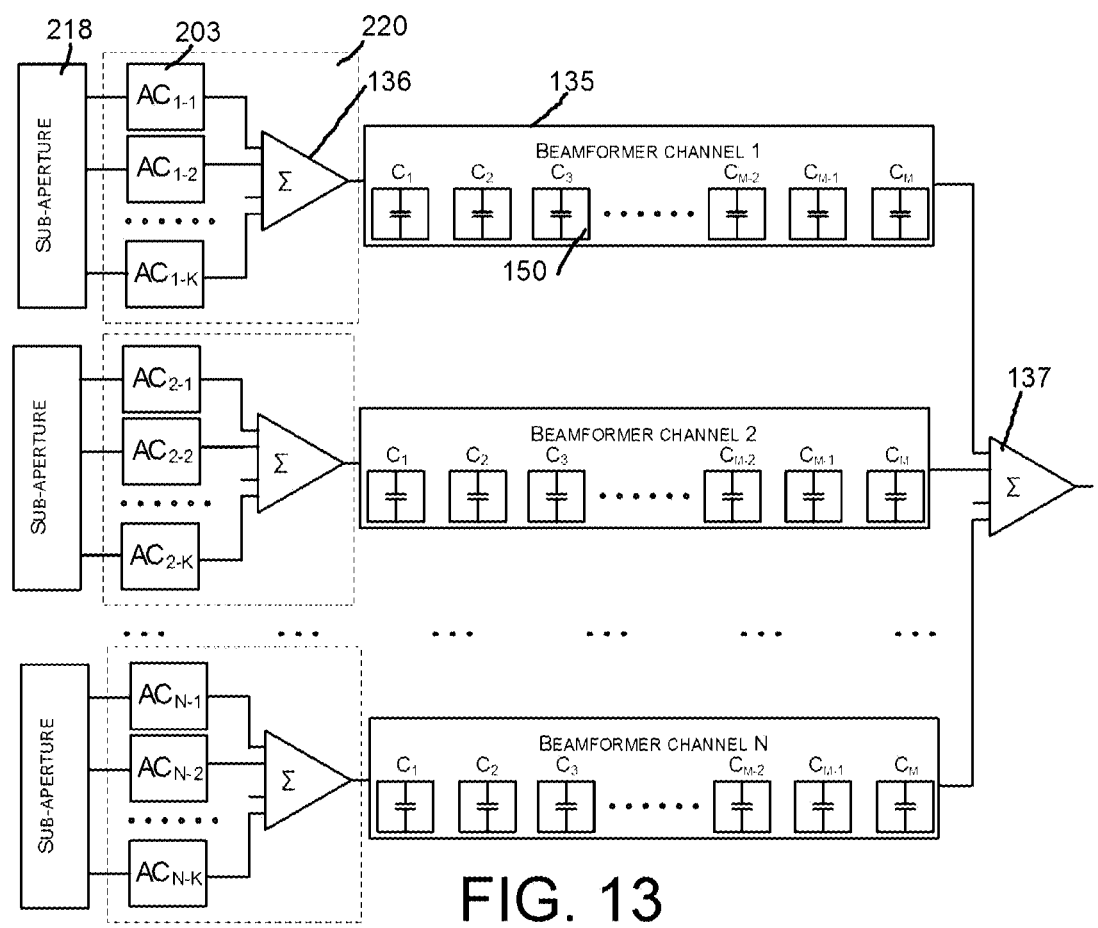
FIG. 13 is a schematic block diagram of sub-aperture transmit and receive beamformer in accordance with one aspect of the present invention.

In the preferred embodiment for 1.5D, 1.75D, and 2D arrays, all elements of the array are divided into groups or sub-apertures 218. Some examples of such sub-apertures are shown on the lower schematics of FIG. 12. The preferred way to select sub-aperture is to assemble an array's elements based on the minimum group delay with respect to the sub-aperture's central element (example on the lowest schematic of FIG. 12) allowing a small number of sample-hold cells in the receive beamformer channel 132 of primary analog channel 203 (FIG. 13), where under the primary (or first) analog channel we understood the channel that connected to the array element. The elements of sub-aperture 218 connect to analog channel 203 (with smaller number of SHC 150) then the content of cells 150 from different channels within sub-aperture is beamformed in the way described above and the output of summing circuit 136 is connected to the second stage beamformer channel 135 which has the same design as beamformer channel 132, but numbered differently to show that first and second stage beamformer channels 132 and 135 are physically different devices that might have different internal structure (e.g. number of cells 150). The contribution of 135 is summed by the second stage summing circuit 137. The output of 137 is the beamformed analog signal put to the input of analog digital converter 120 to create a digitized beamformed RF signal. It is understood that this invention allows for any number of sub-aperture to be formed.

It is also understood that this invention allows for any number of beamforming stages to be implemented, where each collected contribution of lower level sub-apertures become a single channel in the next level sub-aperture until a single beamformed signal is outputted.

In one embodiment for 1.5D, 1.75D, and 2D arrays, all beamforming is done in the ASDR beamformer hardware placed next to the array. In another embodiment, some sub-aperture beamforming could be done in ASDR beamformer next to the array, and then partially beamformed signals are sent via wire or wireless link to the ultrasound machine hardware where the final beamforming is done in ASDR beamformer or in the prior art digital beamformer. The main advantage of such approach is the reduction in number of cables running from the probe to the ultrasound hardware.

Portable Ultrasound Device and ASIC Structure

The ASDR beamformer described in this invention can be used to build compact ultrasound diagnostic devices that combine small size and power consumption with high image quality that results from the high channel count of full aperture and short signal path 109. Such system can be implemented as system-on-the-probe where all hardware necessary for signal acquisition and processing fits in the transducer array handle together with the battery, which wirelessly transmits beamformed and processed signals to the receiver that is connected to a display unit such as a laptop, smartphone, tablet, or a TV set where images are displayed.

Figure 14:
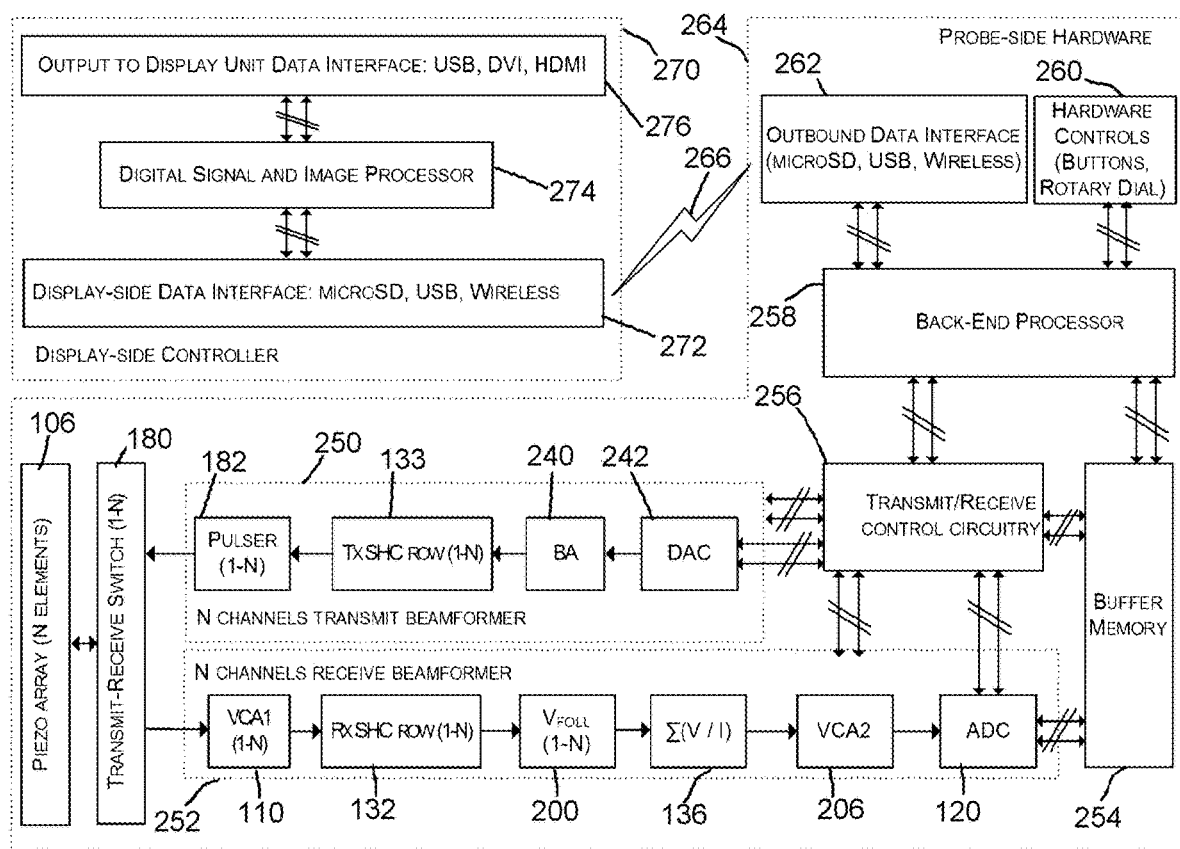
FIG. 14 is a schematic block diagram representing an example of an ASDR ultrasound system in accordance with the present invention.

In one embodiment of such a diagnostic ultrasound system, as it is shown on the example of schematic diagram on FIG. 14, the ASDR beamformer is implemented as one or few integral chips (ICs) that are placed in immediate vicinity of the transducer array 106.

Functioning of the N channels (equal to the number of elements) receive beamformer 252 was described above. In it, the signal from each element of array 106 through T/R switch 180 goes to VCA 110, S/H cells bank 132, then the voltage level of the selected SHC elements through the follower 200 go to the input of summing circuit 136 and via VCA 206 go to the input of ADC 120. The digitized data from the output ADC are written in buffer memory 254.

The transmit-receive control circuitry block 256 controls the flow of data and command in and out of receive beamformers 250, 252, buffer memory 254, and back-end processor 258.

The transmit beamformer 250 writes voltage levels from digital-to-analog converter 242 via buffer amplifier 240 to the transmit SHC array 133. The voltage level samples from 133 are sequentially sent to the pulser 182 to form the high voltage pulse that is sent to the transducer array. The transmit beamforming delays are controlled by the T/R control circuitry block 256. The transmit beamformer DAC 242 may refresh the content of array SHC 133 while the Rx beamformer is in receive mode.

The back-end processor 258 performs initial signal and image processing on raw RF data received from the buffer memory including but not limited to data flow organization (such as creation of line and frame headers), filtering, I/Q, B-mode conversion, Doppler data extraction, data compression, scan image forming, and other typical tasks of the back-end DSP. It also receives and interprets the commands from any buttons and rotary dial controls of the ultrasonic hardware control block 260. Another task of the processor 258 is to organize the flow of information to the outside storage and processing interface block 262, that controls writing ultrasound data to the non-volatile memory storage (such as flash card, SD or a micro-SD), wire based data transfer (such as USB) port and wireless data interface.

The scan data (such as raw RF, Doppler, B-mode, image, volume data) are transferred outside from the probe-side hardware block 264 via wire link or wireless link 266 to the display-side hardware block 270. There, data decoded by the interface 272, the image processed in the block 274 to fit the format of the current display device and outputted to the display interface 276 that transmits the data in the format accepted by the display device through USB, HDMI, DVI, or another input signal port.

In one embodiment of such a system, the ASDR beamformer is built on one ASIC that along with the analog front-end, SHC arrays, digital back end, and control circuitry may include all functional blocks described in block 264 with the exception of the transducer array. In another embodiment, some of the functional blocks or parts of such blocks described in block 264 may be realized separately from the ASDR ASIC. In another embodiment, the system may consist not from a single ASDR ASIC but from a few independent ASDR beamformers working on the single ADC (or each on their own ADC) where each ASDR beamformer has a part of the array 106 as its sub-aperture and final beamforming is done digitally on data streams coming from the multitude of ASDR beamformers. In yet another embodiment few independent ASDR beamformers can be working on the same array 106 with time interleave to achieve higher sampling rates.

It should be noted that the beamformer system is implemented partially in hardware, partially in firmware and partially in software such that precise boundaries between these parts can be established by the needs of the implementation. Further, in all descriptions and schematic diagrams the placement of elements or blocks such as VCA, LNA, voltage followers switches, etc. that are secondary to the understanding of the invention are not strictly followed, assuming that anybody with ordinary knowledge of electronic design would understand their functions would determine where they should be placed in the actual working schematics, their structure, and parameters.

The above description describes an Analog Store Digital Read ultrasound beamforming method for an ultrasound imaging system comprising the steps of: i) Providing an ultrasonic array formed of individual ultrasonic array elements configured for transmission and receiving; ii) Dividing the individual array elements into individual channels, wherein each channel comprises at least one array element; iii) Creating a receiving input signal for each channel from inputs received from each array element of the channel; iv) Sampling each receiving input signal for each channel at a sampling rate and storing the sampled data in a bank of sample-hold cells which are associated with that channel, wherein the bank of sample-hold cells form an analog random access memory for the sampled receiving input signal; v) Selecting at least one sample-hold cell data from at least one channel for each particular output time for each beamforming instance in accordance with a beamforming algorithm; vi) Summing all of the selected sample-hold cell data from the associated channels for the beamforming instance forming an analog beamformed received signal sample for the beamforming instance; and vii) Digitizing the analog beamformed received signal sample.

CONCLUSION

As discussed above the individual channels will generally include, not just the array elements but also the control electronics. Further it is important to note the sampling rate may be fixed or may be variable and may further be independent of the rate the data is read from the cells or the rate such is digitized. The digitized sample is typically stored for further processing as known in the art.

In the Analog Store Digital Read ultrasound beamforming method for an ultrasound imaging system, each channel may comprise only one array element. Further, the creating a receiving input signal for each channel may include processing the inputs from the array elements through at least one voltage controlled amplifier and at least one filter. Additionally, each channel may use less than 40 milliwatts in operation, generally less than 25 milliwatts per channel and typically about 10 milliwatts per channel or even less. Each sample-hold cell may be formed as a capacitor based element. It is noteworthy that selected sample-hold data pass through an analog filter or/and amplifier with variable gain with purpose to assign proper Time Gain Compensation (TGC) values, aperture selection and apodization weighting before the summing for proper signal to noise attenuation.

In the Analog Store Digital Read ultrasound beamforming method the number of sample-hold cells in each bank may be equal to or greater than the sample rate per second times the maximum desired delay for the signal path. Further, a sampling speed for the storing of the sampled data in the bank of sample-hold cells may be independent of a sampling speed for reading the sampled data in the bank of sample-hold cells.

The Analog Store Digital Read ultrasound beamforming method may further include the step of storing at least one shape of a transmission output pulse signal for each transmission channel in a bank of transmission sample-hold cells which are associated with that transmission channel. In one embodiment a single bank of transmission sample-hold cells are associated with multiple transmission channels. Further the method may provide that the same bank of sample-hold cells forms the receiving bank of sample-hold cells and the bank of transmission sample-hold cells for each channel. Alternatively, each channel may be associated with one receiving bank of sample-hold cells and one distinct bank of transmission sample-hold cells.

The Analog Store Digital Read ultrasound beamforming method for an ultrasound imaging system as described above provides that multiple beamforming instances associated with multiple algorithms may be utilized, and may further include the step of storing each of the analog beamformed received signal for each beamforming instances in a bank of beamform sample-hold cells prior to digitizing the analog beamformed received signals.

As summarized above, there are two ways to organize sample memory: 1) During the operation the data are written continuously into the ARAM organized as a ring buffer, such that when the current sample is written into the last address, the write operation folds and begin writing at the first address of the array; or 2) The ARAM memory depth is sufficient to store the whole length of the channel data for the scan line (here the maximum delay is the time required for the signal to travel to the maximum desired scan depth and back to the receiver) providing greater freedom for multiple beamforming The above description defines the transmit beamforming essentially the same way as it describes the receive beamforming. In short a transmit beamformer that forms an ultrasonic pulse by sequentially reading analog sample values stored in transmission bank of sample-hold cells in channels selected by the beamforming algorithm, sending them to the high voltage amplifier or generator connected to the elements of the transmit-receive array where each channel begin to read analog sample values with predefined time delays and sampling rates in accordance to the transmit beamforming algorithms The above description sets forth an Analog Store Digital Read ultrasound beamformer for an ultrasound imaging system comprising: i) An ultrasonic array formed of individual ultrasonic array elements configured for transmission and receiving, wherein the individual array elements are grouped into individual channels, wherein each channel comprises at least one array element; ii) A Receiving input signal control circuitry for creating receiving input signals for each channel from inputs received from each array element of the channel; iii) A plurality of banks of sample-hold cells with each bank of sample-hold cells associated with one channel, wherein the beamformer is configured for sampling each receiving input signal for each channel at a sampling rate and storing the sampled data in one bank of sample-hold cells which are associated with that channel, wherein the bank of sample-hold cells form an analog random access memory for the associated sampled receiving input signal; iv) A beamforming processor configured for selecting at least one sample-hold cell data from at least one channel for each beamforming instance in accordance with a beamforming algorithm; v) An analog summation element for summing all of the selected sample-hold cell data from each channel for each beamforming instance and forming an analog beamformed received signal for the beamforming instance; and vi) An Analog-to-Digital converter for digitizing the analog beamformed received signal.

At least the beamforming processor may be formed as an integrated circuit. Essentially the circuitry implementing the beamforming method may comprise an integrated circuit (IC) such as an application-specific integrated circuit (ASIC).

The above description also defines an Analog Store Digital Read ultrasound beamforming system for an ultrasound imaging system comprising an ultrasonic array formed of individual ultrasonic array elements configured for transmission and receiving, wherein the individual array elements are formed into individual channels, wherein each channel comprises at least one array element and each channel uses less than 40 milliwatts in operation, and generally less than about 25 milliwatts per channel, often less than 15 milliwatts per channel or even less than 10 milliwatts per channel.

The compact ultrasound imaging system formed according to the present invention may send the beamformed signal to an outside display device wirelessly or wired in a display neutral system or manner. The system described provides a compact ASIC, low power device and high channel count (128 or more), with simple scalable architecture. It should be apparent that the beamformer system is implemented partially in hardware, partially in firmware and partially in software such that precise boundaries between these parts can be established by the needs of the implementation.

Further regarding, Sub-aperture beamforming and the secondary Sample-Hold cell bank described above, first, second and tertiary levels (any number of beamforming stages) of sub-aperture beamforming using ARAM beamforming may be provided. An effective way to select sub-aperture is to assemble an array's elements based on the minimum group delay with respect to the sub-aperture's central element. The system may be mix of beamformer methods ARAM, analog, and digital for different stages of sub-aperture beamformer. Further the stages of beamforming can be spatially separated (first stage on the probe and second on the hardware side)—

One advantage of the invention is that it provides significant reduction in the size of the diagnostic ultrasound imaging system such that the hardware build upon ASDR ultrasound beamformer architecture can be placed in one or few application specific integrated chips (ASIC) positioned next to the ultrasound array and the whole diagnostic ultrasound imaging system could fit in the handle of the ultrasonic probe while preserving most of the functionality of a cart-based system.

Another advantage of the invention is that such compact system allows sending data and diagnostic images wirelessly to any image display equipped to receive such transmissions or having such a receiver attached to data ports such as USB or FireWire of the display unit.

Another advantage of the invention is that it provides an improved signal-to-noise ratio by drastic reduction in hardware complexity of the signal path from the transducer elements to the digitizer. Such a shortening of the signal path is achieved by making redundant a number of components of the signal path such as analog high voltage and channel multiplexors, signal cable, and connectors used in prior art to connect ultrasound array with signal processing hardware.

Another advantage of the invention is that it further improves the signal-to-noise ratio, and diagnostic image contrast, and spatial resolution by implementing the full aperture beam formation in which every element of the array operates its' own transmit and receive channel (128 parallel transmit-receive channels for a typical 128 elements 1D array) and thus, the available aperture is equal to the size of the whole array.

Another advantage of the invention is that it uses lower power per channel, thus, allowing for extended time operation on battery power.

Another advantage of the invention is that implementation in one or few ASICs significantly reduce the cost of production of ultrasound system.

Another advantage of the invention is that it has scalable architecture enabling the construction of ultrasound arrays with any number of elements by linear expansion (e.g. one ASIC controls 128 element 1D array, two ASIC-256 elements array, and so on)

Another advantage of the invention is that it improves image quality and reduces the cost of systems built with 1.5D, 1.75D and 2D arrays.

Although the present invention has been described with particularity herein, the scope of the present invention is not limited to the specific embodiments disclosed. It will be apparent to those of ordinary skill in the art that various modifications may be made to the present invention without departing from the spirit and scope thereof. For example the array may be selected in length to provide a whole-scan-line channel storage option, which would not change the fundamentals of operation of the system or method of the invention. The scope of the present invention is defined by the appended claims and equivalents thereto.

What is claimed is:

1. An Analog Store Digital Read ultrasound beamformer for a portable
ultrasound imaging system comprising:
an ultrasonic array formed of individual ultrasonic array elements configured for transmission and receiving, wherein the individual array elements are grouped into individual channels;
a receiving input signal control circuitry for creating receiving input signals for each channel from inputs received from each array element of the channel;
a plurality of banks of sample-hold cells associated with the channels, wherein the beamformer is configured for sampling each receiving input signal for each channel at a sampling rate and storing the sampled data in one bank of sample-hold cells, wherein the bank of sample-hold cells form an analog random access memory for the associated sampled receiving input signal;

a beamforming processor configured for selecting at least one sample-hold cell data from at least one channel for each beamforming instance in accordance with a beamforming algorithm;

an analog summation element for summing all of the selected sample-hold cell data from each channel for each beamforming instance and forming an analog beamformed received signal sample for the beamforming instance; and an analog-to-digital converter for digitizing the analog beamformed received signal, wherein the system is configured for placement in the handle of an ultrasonic probe.

2. The Analog Store Digital Read ultrasound beamformer for an ultrasound imaging system according to claim 1 wherein each channel comprises only one array element, and wherein each channel uses less than 40 milliwatts in operation.

3. The Analog Store Digital Read ultrasound beamformer for an ultrasound imaging system according to claim 1 wherein each sample-hold cell is formed as a capacitor based element and wherein at least part of the beamforming processor is formed as an integrated circuit.

4. The Analog Store Digital Read ultrasound beamformer for an ultrasound imaging system according to claim 1 wherein the number of sample-hold cells in each bank is equal to or greater than the sample rate times the maximum desired delay for the signal path.

5. The Analog Store Digital Read ultrasound beamformer for an ultrasound imaging system according to claim 1 further including a transmission beamformer for storing at least portions of one transmission output pulse signal in a bank of transmission sample-hold cells which are associated with that channel.

6. The Analog Store Digital Read ultrasound beamformer for an ultrasound imaging system according to claim 5 wherein a single bank of transmission sample-hold cells are associated with multiple channels.

7. The Analog Store Digital Read ultrasound beamformer for an ultrasound imaging system according to claim 5 wherein the same bank of sample-hold cells forms the receiving bank of sample-hold cells and the bank of transmission sample-hold cells for at least one channel.

8. The Analog Store Digital Read ultrasound beamformer for an ultrasound imaging system according to claim 5 wherein each channel is associated with one receiving bank of sample-hold cells and one distinct bank of transmission sample-hold cells.

9. The Analog Store Digital Read ultrasound beamformer for an ultrasound imaging system according to claim 1 wherein multiple beamforming instances associated with multiple beamforming algorithms are utilized, and further including a bank of beamform sample-hold cells configured for storing each of the analog beamformed received signal sample for each given beamform prior to digitizing the analog beamformed received signals.

10. An Analog Store Digital Read ultrasound beamforming system for an ultrasound imaging system comprising an ultrasonic array formed of individual ultrasonic array elements configured for transmission and receiving, wherein the individual array elements are formed into individual channels, wherein each channel comprises at least one array element, wherein the Analog Store Digital Read ultrasound beamforming system is formed on at least one integrated circuit.

11. The Analog Store Digital Read ultrasound beamforming system according to claim 10 further including i) a receiving input signal processor in the enclosure for creating receiving input signals for each channel from inputs received from each array element of the channel; ii) A plurality of banks of sample-hold cells in the probe with each bank of sample-hold cells associated with one channel, wherein the beamformer is configured for sampling each receiving input signal for each channel at a sampling rate and storing the sampled data in one bank of sample-hold cells which are associated with that channel, wherein the bank of sample-hold cells form an analog random access memory for the associated sampled receiving input signal; iii) A beamforming processor in the probe configured for selecting at least one sample-hold cell data from at least one channel for each beamforming instance in accordance with a beamforming algorithm; iv) an analog summation element in the probe for summing all of the selected sample-hold cell data from each channel for each beamforming instance forming an analog beamformed received signal for the beamforming instance; v) An analog-to-digital converter for digitizing the analog beamformed received signal; and vi) a transmission beamformer for storing at least portions of one output pulse signal for each channel in a bank of transmission sample-hold cells in the probe which are associated with that channel.

12. The Analog Store Digital Read ultrasound beamformer for an ultrasound imaging system according to claim 10 wherein each channel uses less than 25 milliwatts in operation.

13. The Analog Store Digital Read ultrasound beamformer for an ultrasound imaging system according to claim 10 wherein each channel uses less than 15 milliwatts in operation.

14. The Analog Store Digital Read ultrasound beamforming system according to claim 10 wherein the system is configured for placement in the handle of an ultrasonic probe.

15. The Analog Store Digital Read ultrasound beamforming system according to claim 10 wherein each array element is a piezo-element configured to convert electric energy into mechanical vibrations during the transmit stage and mechanical vibration energy into electric signals during the receive stage.

16. An Analog Store Digital Read ultrasound beamforming system for an ultrasound imaging system comprising an ultrasonic array formed of individual ultrasonic array elements configured for transmission and receiving, wherein the individual array elements are formed into individual channels, wherein each channel comprises at least one array element, wherein each array element is configured to convert electric energy into mechanical vibrations during the transmit stage and mechanical vibration energy into electric signals during the receive stage.

17. The Analog Store Digital Read ultrasound beamforming system according to claim 16 wherein the system is configured for placement in the handle of an ultrasonic probe.

18. The Analog Store Digital Read ultrasound beamforming system for an ultrasound imaging system according to claim 16 wherein each channel uses less than 15 milliwatts in operation.

19. The Analog Store Digital Read ultrasound beamforming system according to claim 16 wherein a beamforming processor for the Analog Store Digital Read ultrasound beamforming system is formed on at least one integrated circuit.

20. The Analog Store Digital Read ultrasound beamforming system according to claim 16 wherein the system is configured for multiple beamforming instances associated with multiple algorithms.

\* \* \* \* \*